(12) United States Patent
Kauffman et al.

(10) Patent No.: US 9,452,421 B2
(45) Date of Patent: Sep. 27, 2016

(54) METHOD FOR MANUFACTURE OF AN ALKANE DEHYDROGENATION CATALYST

(71) Applicant: SAUDI BASIC INDUSTRIES CORPORATION, Riyadh (SA)

(72) Inventors: James William Kauffman, Katy, TX (US); Patricia Ann Hooks, Houston, TX (US); Balamurali Krishna Nair, Sugar Land, TX (US)

(73) Assignee: SAUDI BASIC INDUTRIES CORPORATION, Riyadh (SA)

( * ) Notice: Subject to any disclaimer, the term of this patent is extended or adjusted under 35 U.S.C. 154(b) by 0 days.

(21) Appl. No.: 14/197,562

(22) Filed: Mar. 5, 2014

(65) Prior Publication Data
US 2014/0274673 A1 Sep. 18, 2014

Related U.S. Application Data

(60) Provisional application No. 61/790,183, filed on Mar. 15, 2013.

(51) Int. Cl.
*B01J 37/00* (2006.01)
*B01J 23/02* (2006.01)
(Continued)

(52) U.S. Cl.
CPC ......... *B01J 27/1856* (2013.01); *B01J 37/0201* (2013.01); *B01J 37/08* (2013.01); *C07C 5/333* (2013.01); *C07C 5/48* (2013.01); *B01J 27/13* (2013.01); *C07C 2521/04* (2013.01);
(Continued)

(58) Field of Classification Search
CPC .......... B01J 37/00; B01J 23/02; B01J 23/04; B01J 23/14; B01J 23/18; B01J 23/40; B01J 21/04

USPC ................ 502/208, 213, 224, 226, 227, 229
IPC ............ B01J 37/00, 23/02, 23/04, 23/14, 23/18, B01J 23/40, 21/04
See application file for complete search history.

(56) References Cited

U.S. PATENT DOCUMENTS 3,224,831 A * 12/1965 Stephens .................... 423/213.5
3,502,739 A * 3/1970 Begley et al. ................ 585/624
(Continued)

FOREIGN PATENT DOCUMENTS

| | | |
|---|---|---|
| CN | 87101513 A | 10/1988 |
| EP | 2712675 A1 | 4/2014 |

OTHER PUBLICATIONS

Daniel E. Resasco, "Dehydrogenation by Heterogeneous Catalysts"; School of Chemical Engineering and Materials Science, University of Oklahoma; Encyclopedia of Catalysis; Jan. 2000, 52 pages.
(Continued)

*Primary Examiner* — Patricia L Hailey
(74) *Attorney, Agent, or Firm* — Cantor Colburn LLP (57) ABSTRACT

A method of making a catalyst comprises: mixing three or more catalytically active components with water to form an impregnating solution; contacting a support with the impregnating solution; impregnating the catalytically active components onto the support to form an impregnated support; and calcining the impregnated support to form a catalyst. Another method of making a catalyst comprises: co-impregnating a support with three or more catalytically active components in an impregnating solution to form an impregnated support; and calcining the impregnated support to form the catalyst.

18 Claims, 4 Drawing Sheets

(51) Int. Cl.
    *B01J 23/04*     (2006.01)
    *B01J 23/14*     (2006.01)
    *B01J 23/18*     (2006.01)
    *B01J 23/40*     (2006.01)
    *B01J 21/04*     (2006.01)
    *B01J 27/185*     (2006.01)
    *B01J 37/08*     (2006.01)
    *B01J 37/02*     (2006.01)
    *C07C 5/333*     (2006.01)
    *C07C 5/48*     (2006.01)
    *B01J 27/13*     (2006.01)

(52) U.S. Cl.
    CPC ....... *C07C2523/02* (2013.01); *C07C 2523/14* (2013.01); *C07C 2523/42* (2013.01); *C07C 2523/755* (2013.01); *C07C 2523/89* (2013.01); *Y02P 20/52* (2015.11)

(56) References Cited

U.S. PATENT DOCUMENTS

| | | | |
|---|---|---|---|
| 3,555,105 A * | 1/1971 | Nolan et al. | 585/623 |
| 3,641,182 A * | 2/1972 | Box, Jr. | 585/434 |
| 3,666,412 A * | 5/1972 | Sowards | 423/419.1 |
| 3,789,017 A * | 1/1974 | Walker | 502/213 |
| 3,796,654 A * | 3/1974 | Wilhelm | 208/139 |
| 3,825,612 A * | 7/1974 | Wilhelm | 585/434 |
| 4,401,557 A | 8/1983 | Juguin et al. | |
| 4,416,804 A * | 11/1983 | Antos et al. | 502/213 |
| 5,358,920 A | 10/1994 | Ma et al. | |
| 6,187,984 B1 | 2/2001 | Wu et al. | |
| 6,414,209 B1 | 7/2002 | Herskowitz et al. | |
| 6,635,598 B2 | 10/2003 | Dongara et al. | |
| 7,220,700 B2 | 5/2007 | Lowe et al. | |
| 8,105,971 B2 | 1/2012 | Gaffney et al. | |
| 2012/0209034 A1 | 8/2012 | Zhou et al. | |

OTHER PUBLICATIONS

Wen-Sheng et al., "Effects of Promotors on Catalytic Performance of Pt—Sn/MgAl2O4 Catalyst for Propane Dehydrogenation in the Presence of Steam"; Journal of Natural Gas Chemistry; 1997, V6 (1): 37-43; 7 pages.

KR 20120077688 A English Abstract; Date of Publication: Jul. 10, 2012; 1 page.

International Search Report for International Application No. PCT/US2014/022355; International Filing Date: Mar. 10, 2014; Date of Mailing: Jul. 16, 2014; 5 pages.

Written Opinion of the International Search Report for International Application No. PCT/US2014/022355; International Filing Date: Mar. 10, 2014; Date of Mailing: Jul. 16, 2014; 6 pages.

* cited by examiner

METHOD FOR MANUFACTURE OF AN ALKANE DEHYDROGENATION CATALYST

CROSS-REFERENCE TO RELATED APPLICATION

This application claims the benefit of U.S. Provisional Patent Application Ser. No. 61/790,183 filed Mar. 15, 2013. The related application is incorporated herein by reference.

TECHNICAL FIELD

The present disclosure relates generally to a method of preparing catalysts for use in alkane dehydrogenation.

BACKGROUND OF THE INVENTION

Paraffins are dehydrogenated to olefins, for example, for the manufacture of high octane gasoline, elastomers, detergents, plastics, ion-exchange resins, and pharmaceuticals. The dehydrogenation is accomplished using a catalyst. The activity of the catalyst and the rate of deactivation affect the efficiency of the process. The primary cause of catalyst deactivation is the build-up of coke on the catalyst (e.g., on the catalyst support surface) that leads to the thermal decomposition of the alkane/alkene and eventually inhibits the dehydrogenation reaction.

There is a continuing need to develop new compositions that are more effective catalysts than those currently available in dehydrogenation processes. There is also a need for a catalyst that can be run at higher propane to propylene conversion that produces lower alkane recycle and higher plant throughput and/or that can be operated for longer periods of time during the dehydrogenation cycle between regeneration. Extending the lifetime of the catalyst, would result in a reduction in the amount of overall catalyst and ultimately in the operating costs.

SUMMARY OF THE INVENTION

Disclosed herein are methods of making catalysts and catalysts made therefrom.

In an embodiment, a method of making a catalyst comprises: mixing three or more catalytically active components with water to form an impregnating solution; contacting a support with the impregnating solution; impregnating the catalytically active components onto the support to form an impregnated support; and calcining the impregnated support to form a catalyst.

In another embodiment, a method of making a catalyst comprises: co-impregnating a support with three or more catalytically active components in an impregnating solution to form an impregnated support; and calcining the impregnated support to form the catalyst.

These and other features and characteristics are more particularly described below in view of the figures and detailed description.

DESCRIPTION OF THE DRAWINGS

For a more complete understanding of the present application, reference is now made to the following descriptions taken in conjunction with the accompanying figures in which.

DETAILED DESCRIPTION OF THE INVENTION

The present disclosure relates to a method of making a catalyst for the dehydrogenation of alkanes. The method involves co-impregnating the catalytically active component onto a support, such as an alumina support, in one impregnation step and calcining the catalyst. It was surprisingly found that co-impregnating the catalytically active component onto the support in one step could be successful. This was surprising, for example, since the combined concentration of all of the metals in the combined solution was much higher than step-by-step addition processes that dissolve each metal compound separately and apply them separately. The success of a co-impregnation method of preparing a catalyst was further surprising as it was thought that some of the metal salts might have combined to form insoluble phosphate salts, such as nickel and calcium phosphate, that would give a very different impregnating solution compared to single or double component impregnating solutions. It was surprisingly found that the concentration of the components of the present disclosure could be as high as eight times the molar concentration as compared to prior art. For example, Table 1 shows the concentration conditions of the catalyst prepared in the step-by-step addition method of Example 1 of U.S. Pat. No. 6,414,209, relative to the concentration conditions of Example 1 of the present disclosure, where the concentration, mol/L, is moles per liter and wt % is weight percent. It was unexpected that when using these metals at optionally high concentrations and in combination with each other in forming the catalyst that such a catalyst could perform well.

TABLE 1

| Component | U.S. Pat. No. 6,414,209 | | Current Patent Application | |
|---|---|---|---|---|
| | Concentration (mol/L) | Concentration (wt %) | Concentration (mol/L) | Concentration (wt %) |
| Ca | 0.56 | 2.84 | 1.67 | 2.85 |
| Ni | 0.16 | 1.12 | 0.17 | 1.10 |
| P | 0.30 | 5.19 | 1.85 | 4.08 |
| Sn | 0.13 | 1.85 | 0.70 | 1.77 |
| HCl | 0.10 | 0.15 | 0.50 | 0.13 |
| Pt | 0.026 | 0.66 | 0.21 | 0.75 |

Figure 1:
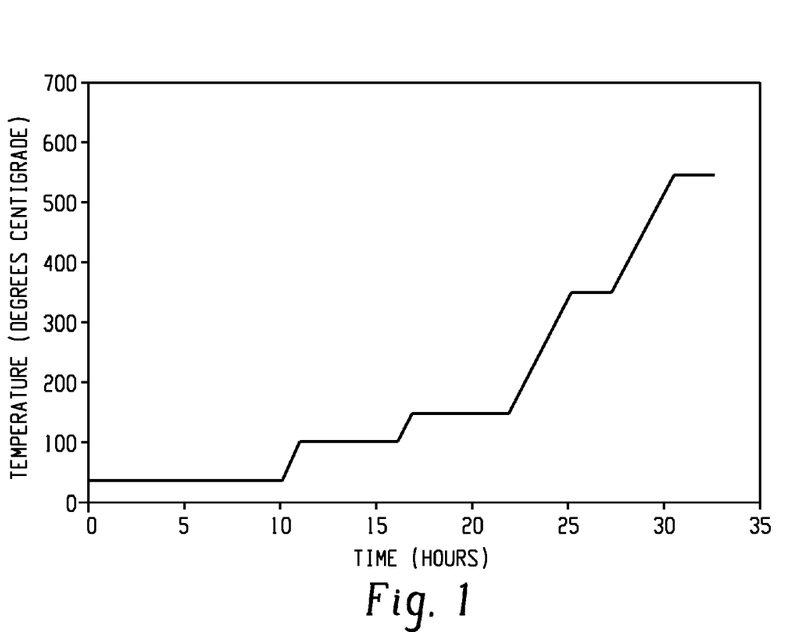
FIG. 1 is a graphical illustration of a single impregnation/calcination step for a reference method.

It was further found that a catalyst prepared by co-impregnating the catalytically active component has the further benefit of a significantly reduced synthesis time as compared to the repetition of the impregnation and calcination cycle that typically occurs for each component in prior processes. For example, U.S. Pat. No. 6,414,209, discloses that one impregnation and calcination cycle takes over 30 hours as illustrated in FIG. 1 and further discloses that this impregnation and calcination step is repeated five more times, once for each subsequent component, totaling more than two weeks' time to produce a single catalyst. Significant time savings can be observed when preparing a catalyst as prepared by co-impregnating the catalytically active component in one impregnation and calcination step that can result in a final catalyst in less than one day.

Surprisingly, a catalyst, as prepared by co-impregnating the catalytically active component onto the support, can result in one or more of enhanced low-coking properties, excellent conversion, excellent selectivity, and a stable lifetime as compared to a commercial catalyst tested under the same conditions. Economic savings from this catalyst can be observed in paraffin conversion, for example, of propane to propylene, in (i) that the dehydrogenation can be performed at a higher conversion resulting in lower alkane recycle and higher plant throughput and/or (ii) that the catalyst can be used for longer periods of time between regenerations, which would extend the lifetime of the catalyst, thus reducing overall catalyst and operating costs. These economic savings are ultimately obtained due to the reduced coke build-up on the catalyst, in addition to the reduced synthesis time of the catalyst.

The catalyst can be prepared, for example, by preparing an aqueous impregnation solution comprising a catalytically active component (that can comprise three or more catalytically active components), impregnating the catalytically active component onto a support to form an impregnated support. The impregnation solution can be applied to the support within 1 hour (hr), specifically, less than or equal to 45 minutes (min), more specifically, less than or equal to 20 minutes of being prepared. The impregnation solution can be constantly stirred prior to being applied to the support. The support can be immersed in the impregnating solution under optional agitation for a period of time sufficient to impregnate the support. The impregnation time can be, for example, up to 10 hours, e.g., 0.5 to 10 hours and can occur at room temperature. The support can be immersed in the impregnating solution, with or without agitation (e.g., stirring) for all or for a portion of the impregnation period.

After impregnation, the catalytically active component can be located on the surface of the support including on the surface of any pores located therein and the framework of the support can remain free of the catalytically active component.

Figure 2:
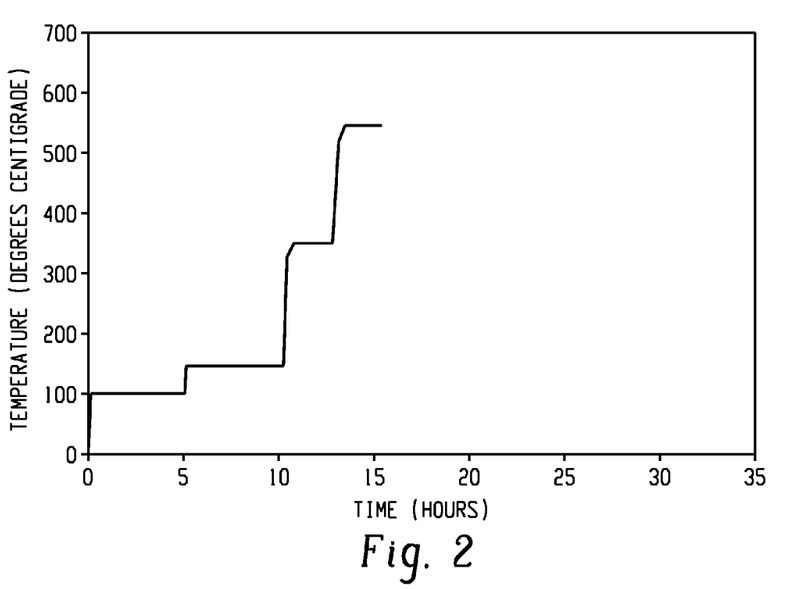
FIG. 2 is a graphical illustration of an exemplary calcination step.

The impregnated support can then be dried and/or calcined to remove water and other volatile materials, and to form the catalyst. The drying can occur at room temperature or at an elevated temperature of 25 to 500 degrees Celsius (° C.), more specifically, 120 to 200° C., e.g., for a period of time sufficient to dry the impregnated support. The drying time can be 0.5 to 10 hours, specifically, 0.5 to 5 hours. The calcining can occur at a temperature of 200 to 1,000° C., specifically, 500 to 800° C., more specifically, 550 to 700° C., e.g., for a period of time sufficient for calcination. The calcination can be for 1 to 20 hours, specifically, 5 to 15 hours, and more specifically, 8 to 12 hours. The calcination can occur at various temperatures for different amounts of time, for example, the calcination can occur as illustrated in FIG. 2. The calcining may include ramping the temperature in various stages. An example of a calcination profile includes increasing the catalyst bed temperature at 5° C./minute to 100° C. and soaking in air for 5 hours; increasing the catalyst bed temperature at 5° C./minute to 150° C. and soaking in air for 5 hours; increasing the catalyst bed temperature at 5° C./minute to 340° C.; increasing the catalyst bed temperature at 1° C./minute to 350° C. and soaking in air for 2 hours; increasing the catalyst bed temperature at 10° C./minute to 540° C.; increasing the catalyst bed temperature at 1° C./minute to 550° C. and soaking in air for 2 hours. Any commercial calciner can be used, such as fixed bed or rotating calciners. Calcination can be performed in various atmospheres such as in air, oxygen, inert atmosphere (e.g., nitrogen), steam, or mixtures thereof. The total preparation time of the catalyst can be, for example, 1 to 60 hours, specifically, 5 to 40 hours. After calcination, the catalyst can be cooled (actively and/or passively) to room temperature.

The impregnation solution can comprise water and two or more catalytically active components, specifically, three or more catalytically active components, where the specific components are dependent upon the reaction that the catalyst is intended to catalyze, e.g., based upon various combinations of elements from Groups 1 to 17 of the periodic table of elements. For example, the catalytically active component can comprise platinum, iridium, germanium, tin, lead, gallium, indium, thallium, lithium, sodium, potassium, rubidium, cesium, francium, iron, cobalt, nickel, palladium, phosphorus, beryllium, magnesium, calcium, strontium, barium, radium, chlorine, a lanthanum series element or a combination comprising one or more of the foregoing. The catalytically active component can comprise platinum and/or iridium as a promoter. The catalytically active component can comprise an element from Groups 2, 10, 14, 15, or a combination comprising one or more of the foregoing, specifically, a combination comprising two or more of the foregoing. The catalytically active component can comprise platinum, tin, nickel, calcium, and phosphorus. Generally, negative components such as nickel, phosphorus, and calcium are a problem in alkane dehydrogenation as they are believed to increase coking. However, it was unexpectedly discovered that nickel, phosphorus, and calcium could be successfully used for alkane dehydrogenation due to the improved properties of the present catalyst (e.g., resistance to coking and/or facile decoking).

The catalytically active component can be added to the mixture as in any form such that it is water soluble. For example, the catalytically active component can be added as one or more of a metal salt, such as nitrate, ammonium, or chloride salts and can be hydrated salts; salts of organic acids, carbonates, or oxides; or a combination comprising one or more of the foregoing. For example, when phosphorus is included, the phosphorus component can comprise an acid such as phosphoric acid, hypophosphorous acid, phosphorous acid, peroxomonophosphoric acid, hypophosphoric acid, pyrophosphoric acid, triphosphoric acid, and the like, as well as combinations comprising at least one of the foregoing. The phosphorus component can comprise phosphoric acid.

The pH of the catalytically active component can be adjusted by addition of an acid, such as hydrochloric acid, nitric acid, sulfuric acid, acetic acid, oxalic acid, and formic acid, or a base such as sodium hydroxide, ammonium hydroxide, potassium hydroxide, sodium bicarbonate, and potassium bicarbonate. The pH can be acidic in order to prevent metal hydroxides from forming, which could cause precipitation of the some of the metal species, which could result in lower metal dispersion on the alumina surface and consequently lower catalyst performance. The pH can be −2 to 6, specifically, −2 to 4, more specifically, −1 to 0.

The concentration of the catalytically active components in the impregnating solution can vary widely, for example, the concentration of the catalytically active components can be 0.01 to 40 molar, specifically, 0.01 to 10 molar, depending on the solubility of the particular materials employed. For example, based upon a total weight of the mixture, the mixture can comprise: 0.2 to 2 weight percent (wt %) platinum, specifically, 0.5 to 1.5 wt % platinum, and more specifically, 0.7 to 1.2 wt % platinum; 0.2 to 5 wt % tin, specifically, 1 to 4 wt % tin, and more specifically, 2 to 3.5 wt % tin; 0.1 to 4 wt % nickel, specifically, 0.5 to 2.5 wt % nickel, and more specifically, 0.8 to 1.5 wt % nickel; and 0.1 to 5 wt % calcium, specifically, 1 to 5 wt % calcium, and more specifically, 1.2 to 2.0 wt % calcium. The phosphorus component can be present in an amount of 0.5 to 4 wt %, specifically, 0.7 to 3 wt %, and more specifically, 0.8 to 1.5 wt %, based upon a total weight of the mixture.

The support can comprise a heat-resistant oxide or a mixed oxide. The oxide can comprise one or more of zirconium dioxide, zinc oxide, aluminum oxide, silicon dioxide, titanium dioxide, magnesium oxide, lanthanum oxide, cerium oxide, and the like. The support can, for example, be a large pore support, e.g., having an average pore diameter range of greater than or equal to 90 angstroms (Å), for example, 90 to 250 angstroms (Å). Alternatively, or in addition, the support can have an average surface area, e.g., greater than or equal to 50 meter squared per gram ($m^2/g$), such as, 50 to 150 $m^2/g$. The support can be a calcined support. Prior to forming the catalyst, the support can be treated with, for example, the sources of the various materials described above.

The support can comprise an alumina support. The alumina support can be any form of crystalline alumina material, such as η-alumina, θ-alumina, χ-alumina, γ-alumina materials, or a combination comprising one or more of the foregoing. Those having a large surface area can be particularly useful, where the alumina support can have a surface area of 50 to 150 $m^2/g$ and a pore diameter range of 90 to 250 angstroms to obtain a desired pore size distribution. The alumina support can be thermally stabilized by calcining prior to or during the formation of the final catalyst.

The support can be an extrudate that can be obtained from a catalyst manufacturer or can be made by preparing a precursor, forming it into the desired catalyst shape, and calcining the precursor to give the final support. The support can be configured in various shapes and sizes. For example, the shape and size can be cylindrical in shape with a ⅛ inch (1.6 mm) diameter that can vary in length, such as ⅛ inch (1.6 mm) or less to up to several inches. In certain applications, the shape and size can be spherical or tablet-shaped or configured into other shapes, such as a star shape, where the thickness of the particle can be of various thicknesses, which can be greater than or less than ⅛ inch (3.1 mm) thick (e.g., 1/16 inch (1.6 mm) to ½ inch (12.7 mm)) The support can be calcined prior to incorporation of the catalytically active component to ensure it has the proper surface area and pore structure and crystalline phase. The support can be dried (e.g., 120° C. for 2 hr) before the impregnation if desired.

The final catalyst can comprise the catalytically active component(s) in an amount of 0.1 to 15 wt %, specifically, 3 to 10 wt %, and more specifically, 5 to 8 wt %, based upon a total weight of the final catalyst (i.e., after drying and calcination). For example, the final catalyst can comprise 0.1 to 20 wt % phosphorus, 0.1 to 75 wt % tin, and 0.1 to 10 wt % of Group 1 and/or 2 metals, based upon a total weight of the catalytically active component(s). The final catalyst can comprise 0.2 to 25 wt %, specifically, 0.5 to 1.5 wt %, more specifically, 0.7 to 1.2 wt % platinum; 0.2 to 5 wt %, specifically, 1 to 4 wt %, more specifically, 2 to 3.5 wt % tin; 1 to 3 wt %, specifically, 1 to 3 wt %, more specifically, 1.1-1.5 wt % phosphorus; 0.1 to 5 wt %, specifically, 1 to 5 wt %, more specifically, 1.2 to 2.0 wt % calcium; 0.1 to 2 wt %, specifically, 0.12 to 1 wt %, more specifically, 0.12 to 0.6 wt % chlorine; 0.1 to 4 wt %, specifically, 0.5 to 2.5 wt %, more specifically, 0.8 to 1.5 wt % nickel; or a combination comprising one or more of the foregoing.

The catalyst can be used in a dehydrogenation process, including oxidative dehydrogenation, and can be used to convert hydrocarbons such as paraffin and/or alkane hydrocarbons into the corresponding olefins. The conversion conditions can be those dehydrogenation reaction conditions useful to form dehydrogenated hydrocarbon products, such as a propane feed that is dehydrogenated to form propylene. The process can be carried out by forming a mixture, preferably preheated, of hydrocarbon feed, steam, if used, and oxygen and/or oxygen-containing gases, if used, and passing this mixture over the catalyst at the desired temperature. A steam or water co-feed can be used in the reaction with the hydrocarbon feed. The steam or water can act as a carrier gas to facilitate introduction of the hydrocarbon into the reactor. The steam can act to carry heat into the reactor since the dehydrogenation is an endothermic reaction and can act to minimize coking, for example, by at least partially removing coke and/or by inhibiting coke formation on the catalyst. The steam can also serve to dilute the hydrocarbon feed so the catalyst is not quickly coked and the reactor is not cooled too much due to the endothermic dehydrogenation reaction. Steam can also serve as a diluent that can shift the equilibrium conversion to higher values. In certain applications, the hydrocarbon/water molar feed ratio can be 1:1 to 10:1, specifically, 1:2 to 1:6, and more specifically, 1:3 to 1:5. The molar ratio of water vapor to the paraffin hydrocarbons can be 0.5:1 to 10:1, specifically, to 1:1 to 6:1. The catalyst can be used with feed materials that contain hydrocarbons of the group comprising $C_{2-6}$ paraffins.

The hydrocarbon feed stream can optionally be mixed with steam and put into contact with the present catalyst at a temperature of 300 to 750° C., and a pressure of 0.01 to 17 bar (absolute), specifically, from 1 to 5 bar (absolute). Recycle of unconverted organic compound feed can be employed if desired; however, the conversion rates and selectivity of this disclosure are generally sufficiently high to justify a single pass operation, if, for example, the product streams can be used without separation steps in a subsequent operation, such as polymerization.

The dehydrogenation reaction can be a non-oxidative dehydrogenation reaction wherein the reaction is carried out in an oxygen-free or substantially oxygen-free (i.e., no oxygen gas or $O_2$) environment. Furthermore, the reaction can be carried out without any hydrogen gas ($H_2$) co-feed, as is used in some dehydrogenation reactions. Any diluents, which can be an inert diluent such as helium, can also be used in the reaction.

The feed streams can be preheated and introduced into the reactor at a temperature of 200 to 300° C. The hydrocarbon, steam, and diluent feed can be introduced into the reactor at a gas hourly space velocity (GHSV) of 2,100 to 4,500 $hr^{-1}$, more specifically, 3000 to 3500 $hr^{-1}$.

Because the dehydrogenation reaction is endothermic, heat input can be required to maintain the reaction. The dehydrogenation reaction can be carried out in a tube-type fixed bed reactor that is provided with a heat source to maintain suitable reaction temperatures. Other suitable reactors can be used however. The reaction temperature can be 525 to 610° C., specifically, 545 to 595° C. If a higher purity propylene is desired, then the product stream can be processed through a purification unit.

Set forth below are some embodiments of the method for making the catalyst disclosed herein, and the catalyst made thereby.

Embodiment 1

A method of making a catalyst, comprising: mixing three or more catalytically active components with water to form an impregnating solution; contacting a support with the impregnating solution; impregnating the catalytically active components onto the support to form an impregnated support; and calcining the impregnated support to form a catalyst.

Embodiment 2

The method of Embodiment 1, wherein the contacting occurs in less than or equal to 1 hour of forming the impregnating solution.

Embodiment 3

A method of making a catalyst, comprising: co-impregnating a support with three or more catalytically active components in an impregnating solution to form an impregnated support; and calcining the impregnated support to form the catalyst.

Embodiment 4

The method of Embodiment 3, wherein the co-impregnating occurs in less than or equal to 1 hour of forming the impregnating solution.

Embodiment 5

The method of any of Embodiments 1-4, wherein the catalytically active component comprises elements from one or more of Groups 2, 10, 14, and 15.

Embodiment 6

The method of any of Embodiments 1-5, wherein the catalytically active component comprises platinum, tin, nickel, phosphorus, calcium, or a combination comprising at least one of the foregoing.

Embodiment 7

The method of any of Embodiments 1-6, wherein the support comprises a calcined alumina support.

Embodiment 8

The method of any of Embodiments 1-7, wherein the total preparation time of the catalyst is 1 to 30 hours.

Embodiment 9

The method of any of Embodiments 1-8, wherein the catalyst comprises 0.1 to 20 wt % phosphorus, 0.1 to 75 wt % tin, and 0.1 to 10 wt % of Group 1 and/or 2 metals, based upon a total weight of the catalytically active component(s).

Embodiment 10

The method of any of Embodiments 1-9, wherein the catalyst comprises 0.2 to 25 wt % platinum, 0.2 to 5 wt % tin, 1 to 3 wt % phosphorus, 0.1 to 5 wt % calcium, 0.1 to 2 wt % chlorine, and 0.1 to 4 wt % nickel, based upon a total weight of the catalyst.

Embodiment 11

The method of any of Embodiments 1-10, wherein the catalyst comprises 0.5 to 1.5 wt % platinum, 1 to 4 wt % tin, 1 to 2 wt % phosphorus; 1 to 5 wt % calcium, 0.12 to 1 wt % chlorine, 0.5 to 2.5 wt % nickel, based upon a total weight of the catalyst.

Embodiment 12

The method of any of Embodiments 1-11, wherein the catalyst comprises 0.7 to 1.2 wt % platinum, 2 to 3.5 wt % tin, 1.1 to 1.5 wt % phosphorus, 1.2 to 2.0 wt % calcium, 0.12 to 0.6 wt % chlorine, 0.8 to 1.5 wt % nickel, based upon a total weight of the catalyst.

Embodiment 13

The method of any of Embodiments 1-12, wherein the calcining is at a temperature of 200 to 1,000° C. for a total period of 1 to 20 hours.

Embodiment 14

The method of any of Embodiments 1-13, wherein the calcining is at a temperature of 500 to 800° C. for a total period of 5 to 15 hours.

Embodiment 15

The method of any of Embodiments 1-14, wherein the calcining is at a temperature of 550 to 700° C. for a total period of 8 to 12 hours.

Embodiment 16

The method of any of Embodiments 1-15, wherein the catalyst is made in a period of less than or equal to 60 hours.

Embodiment 17

The method of any of Embodiments 1-16, wherein the catalyst is made in a period of less than or equal to 40 hours.

Embodiment 18

The method of any of Embodiments 1-17, wherein the catalyst is made in a period of less than or equal to 30 hours.

Embodiment 19

The method of any of Embodiments 1-18, wherein the contacting occurs in less than or equal to 45 minutes, or less than or equal to 20 minutes, of forming the impregnating solution, and optionally wherein the impregnation solution is constantly stirred prior to being applied to the support.

Embodiment 20

The method of any of Embodiments 1-19, wherein the impregnating is for a period of less than or equal to 10 hours, or 0.5 to 10 hours, or less than or equal to 5 hours.

Embodiment 21

The method of any of Embodiments 1-20, wherein the calcining is performed with a calcination profile, wherein the calcination profile includes increasing a catalyst bed temperature by less than or equal to 10° C./minute to 100° C. and soaking for less than or equal to 10 hours; increasing the catalyst bed temperature by less than or equal to 10° C./minute to 150° C. and soaking for less than or equal to 10 hours; increasing the catalyst bed temperature by less than or equal to 10° C./minute to 340° C.; increasing the catalyst bed temperature by less than or equal to 5° C./minute to 350° C. and soaking for less than or equal to 5 hours; increasing the catalyst bed temperature by less than or equal to 15° C./minute to 540° C.; increasing the catalyst bed temperature by less than or equal to 5° C./minute to 550° C. and soaking for less than or equal to 5 hours.

Embodiment 22

The method of any of Embodiments 1-21, wherein the calcining is performed with a calcination profile, wherein the calcination profile includes increasing a catalyst bed temperature by 2° C./minute to 8° C./minute up to 100° C. and soaking for 2 to 8 hours; increasing the catalyst bed temperature by 2° C./minute to 8° C./minute up to 150° C. and soaking for 2 to 8 hours; increasing the catalyst bed temperature by 2° C./minute to 8° C./minute up to 340° C.; increasing the catalyst bed temperature by 1° C./minute to 4° C./minute up to 350° C. and soaking for 0.5 to 3 hours; increasing the catalyst bed temperature by 8° C./minute to 12° C./minute up to 540° C.; increasing the catalyst bed temperature by 1° C./minute to 4° C./minute up to 550° C. and soaking for 0.5 to 3 hours.

Embodiment 23

The method of any of Embodiments 1-22, wherein the calcining is performed with a calcination profile that includes increasing the catalyst bed temperature at 5° C./minute to 100° C. and soaking in air for 5 hours; increasing the catalyst bed temperature at 5° C./minute to 150° C. and soaking in air for 5 hours; increasing the catalyst bed temperature at 5° C./minute to 340° C.; increasing the catalyst bed temperature at 1° C./minute to 350° C. and soaking in air for 2 hours; increasing the catalyst bed temperature at 10° C./minute to 540° C.; increasing the catalyst bed temperature at 1° C./minute to 550° C. and soaking in air for 2 hours.

Embodiment 24

The method of any of Embodiments 21-23, wherein the soak is in air.

Embodiment 25

The method of any of Embodiments 1-24, wherein the catalytically active component comprises four or more catalytically active components.

Embodiment 26

The method of any of Embodiments 1-25, wherein the catalytically active component comprises five or more catalytically active components.

Embodiment 27

The method of any of Embodiments 1-26, wherein the catalytically active component comprises five or more catalytically active components.

Embodiment 28

The method of any of Embodiments 1-27, wherein the catalytically active component comprises six or more catalytically active components.

Embodiment 29

The method of any of Embodiments 1-28, wherein the catalytically active component comprises seven or more catalytically active components.

Embodiment 30

A catalyst formed by the method of any of Embodiments 1-29.

Embodiment 31

The catalyst of Embodiment 30, wherein the catalyst has a selectivity for alkane dehydrogenation of greater than 90% to 95% and was maintained for greater than 140 hours.

Embodiment 32

The catalyst of any of Embodiments 30-31, wherein the catalyst has a percent conversion of alkanes of greater than or equal to 50% for greater than or equal to 75 hours.

Embodiment 33

The catalyst of any of Embodiments 30-32, wherein the catalyst has a percent conversion of alkanes of greater than or equal to 50% for greater than or equal to 110 hours.

Embodiment 34

The catalyst of any of Embodiments 30-33, wherein the alkane dehydrogenation is the reaction of propane to propylene.

The following examples are provided to illustrate the method of preparing the catalyst of the present disclosure. The examples are merely illustrative and are not intended to limit methods made in accordance with the disclosure to the materials, conditions, or process parameters set forth therein.

EXAMPLES

Example 1

Catalyst Preparation

An impregnating solution was formed from the components listed in Table 2, where the amounts are listed in either grams (g) or milliliters (mL), to form a 1 wt % phosphorus mixture with a Ca:Ni:P ratio of 0.9:0.1:1.

TABLE 2

| Component | Amount added |
|---|---|
| $H_3PO_4$ | 0.84 g |
| HCl | 0.2 mL |
| Water | 3.95 mL |
| $Ni(NO_3)_2 \cdot 6H_2O$ | 0.20 g |
| $SnCl_2 \cdot 2H_2O$ | 0.62 g |
| $Ca(NO_3)_2 \cdot 4H_2O$ | 1.56 g |
| $H_2PtCl_6$, aqueous, 20% Pt | 0.5 mL |

14 g of calcined alumina support, SCl eta-alumina, (commercially available from Sud-Chemie, Louisville, Ky.) was added to the impregnating solution and the mixture was allowed to sit for several minutes under agitation until the alumina support was impregnated. The impregnated support was calcined at 500° C. in air for 2 hours, to form the catalyst. The catalyst was cooled to room temperature and stored in dry nitrogen.

Example 2

Comparison of the Dehydrogenation of Propane to Propylene Ability of the Catalyst of Example 1 to a Commercially Available Catalyst Two dehydrogenation reactions of propane to propylene were performed using the catalyst of Example 1, Catalyst a, and a commercially available catalyst, Catalyst b. The commercially available catalyst, was a commercial propane dehydrogenation catalyst and was chosen as it is a platinum on alumina catalyst that is widely commercially used for dehydrogenation reactions that generally comprises 0.3 to 1.5 wt % platinum.

The time-on-stream was eight hours with a one hour regeneration period. The concentration of $O_2$ used was 2.8 mole % with a flow of 20 standard cubic centimeters per minute (ccm). Regeneration time was limited to 60 minutes. There was always a 5° C. temperature difference between set temperature of the furnace and the bed thermocouple during nitrogen ($N_2$) purge cycles. During other cycles (dehydrogenation and regeneration), this difference is dictated by the endothermicity or exothermicity of the reaction in addition to the above. The set point was kept at 550° C. for the dehydrogenation and reduced to 485° C. for the regeneration. The changes in the temperature profile were made at the start of the purge cycle (with $N_2$) just before the dehydrogenation and regeneration respectively. This ensured the temperatures were at a steady state before the start of dehydrogenation and regeneration. The initial 1 h shown in FIG. 3 was the purge cycle with $N_2$.

Figure 3:
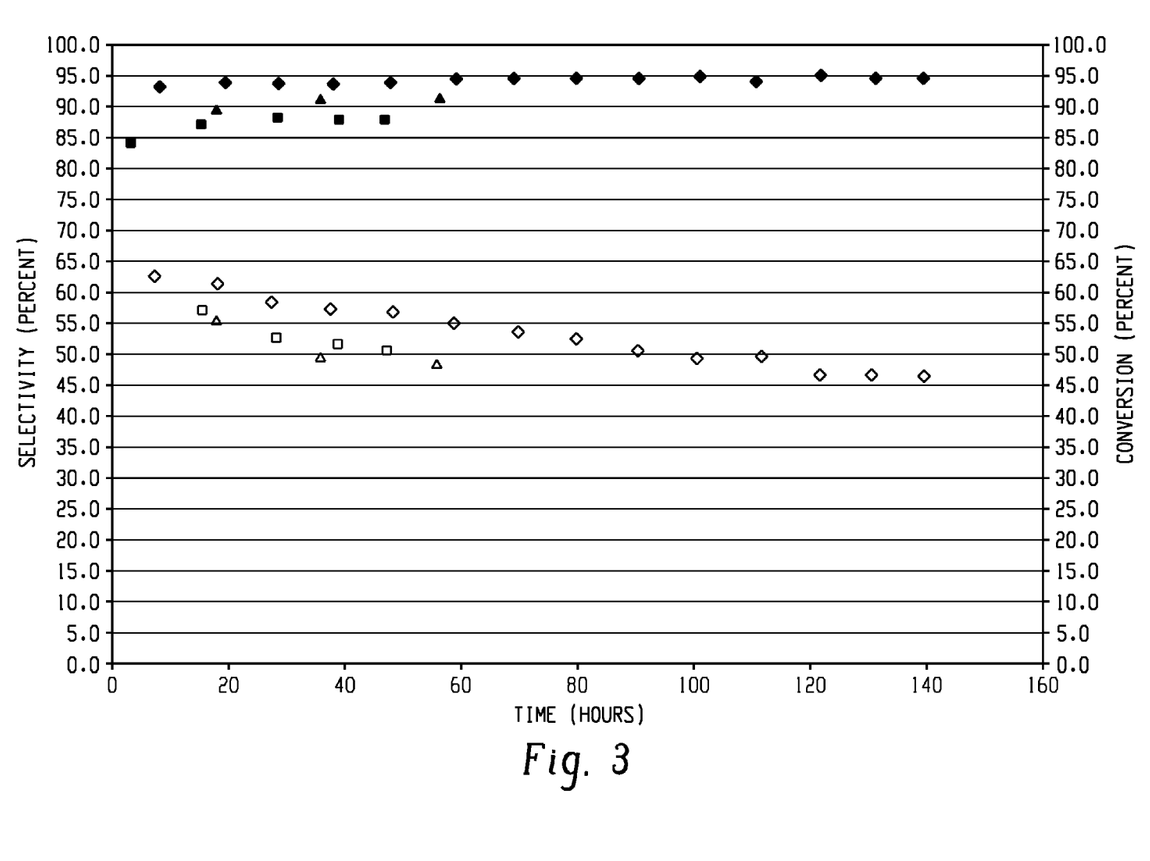
FIG. 3 is a graphical illustration of selectivity and conversion of Catalyst a and commercial Catalyst b of Example 2.

FIG. 3 shows the test results for the catalyst of Example 1 as denoted by the diamonds (Catalyst a) and test results from two runs using the commercial catalyst as denoted by the squares and triangles (Catalyst b), where each data point represents a seven hour dehydrogenation period.

Surprisingly, Catalyst a (open diamonds) showed much better stability than the commercial platinum catalyst, Catalyst b (open squares and triangles), as Catalyst a exhibited less of a decline in conversion with time and was closer to the equilibrium conversion line (the theoretical limit at 70% conversion), see FIG. 3. This figure shows that Catalyst b drops in conversion rapidly while Catalyst a does not exhibit such a rapid decrease in conversion indicating there was slower build-up coke on the catalyst surface with better catalyst. Without being bound by theory, the Applicants believe that the conversion drops as coke builds up on the catalyst surface and covers the platinum particles, preventing the dehydrogenation reaction from occurring. Therefore, the Applicants believe that a more rapid decrease in conversion indicates a more rapid build-up of coke on the catalyst surface.

It should further be noted that the reactions were run at the high temperature of 595° C. in order to accelerate any coking that would otherwise occur on the catalyst and still the catalyst of Example 1 was able to resist coke build-up. While it is expected that the lifetime of the catalyst will further increase at lower operating temperature, the ability of the catalyst of Example 1 to operate at higher temperatures advantageously allows for a higher conversion to propylene.

Furthermore, although both catalysts were able to produce greater than 90% selectivity, it is clear from the graph in FIG. 3 that at the same catalyst loading, with the same process conditions, that Catalyst a (solid diamonds) showed better selectivity at all time points and was almost able to achieve selectivities of 95%. Additionally, a selectivity for the dehydrogenation reactions of propane to propylene of greater than 90% to 95% was maintained for greater than 140 hours. The solid squares and triangles represent two runs with samples of Catalyst b. As is clear, the present catalyst (Catalyst a, the open diamonds) can maintain a percent conversion of propane to propylene of greater than or equal to 50% for greater than or equal to 75 hours, specifically, greater than or equal to 50% for greater than or equal to 110 hours.

Example 3

Figure 4:
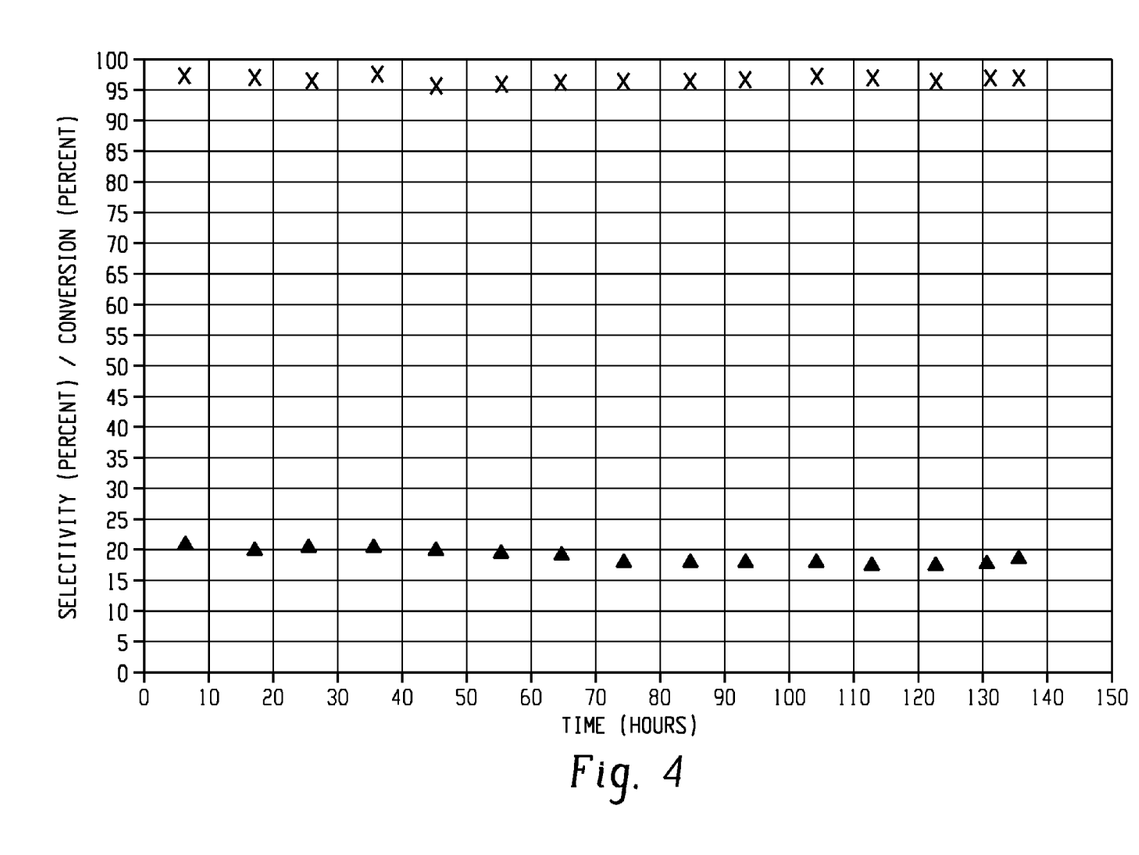
FIG. 4 is a graphical illustration of selectivity and conversion of Catalyst c of Example 3.
Figure 5:
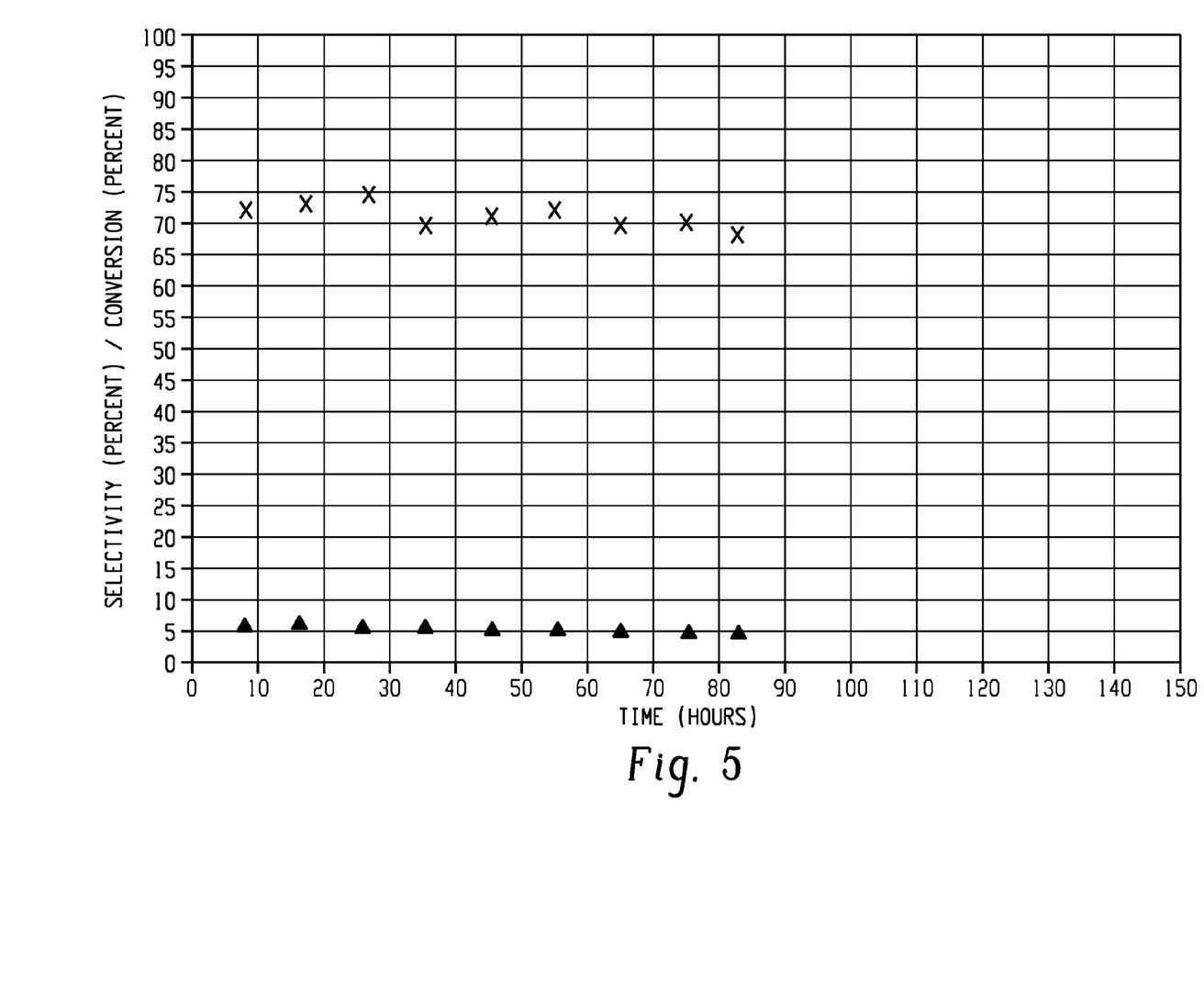
FIG. 5 is a graphical illustration of selectivity and conversion of Catalyst d of Example 3.

Comparison of the Dehydrogenation of Propane to Propylene Ability of a Co-Impregnation Catalyst to a Catalyst Prepared by a Step-by-Step Addition Method Two catalyst samples, Catalyst c and Catalyst d were prepared using the same composition shown in Table 2, except that Catalyst c was prepared via a co-impregnation method of the present disclosure, while Catalyst d was prepared using the elements as disclosed in Table 2 via the step-by-step addition method as described in U.S. Pat. No. 6,414,209. Specifically, Catalyst c was prepared by introducing the impregnating solution comprising the elements as listed in Table 2. The impregnation of the catalyst was calcined according to the profile described in FIG. 2. Catalyst d was prepared using the calcination profile as illustrated in FIG. 1, which includes the approximately 32 hours long calcination shown in repeated five times after separate impregnation of the components calcium and nickel, phosphate, tin, platinum, and potassium. Each calcination was followed by a cooling period of up to 1 to 10 hours as required after a high temperature calcination leading to a very long total preparation time. The conversion (illustrated with triangles) and selectivity (illustrated with "X") results using the conditions as described in Example 2 for Catalysts c and d are shown in FIGS. 4 and 5, respectively. Clearly the conversion and selectivity results are much lower for Catalyst d as compared to Catalyst c. For example, Catalyst c had a nearly 300% improvement in conversion percent (from around 5% for Catalyst d to over 15% for Catalyst c). Furthermore, the selectivity also showed an improvement, e.g., a greater than 25% improvement; below 75% for Catalyst d versus over 95% for Catalyst c.

The terminology used herein is for the purpose of describing particular embodiments only and is not intended to be limiting. It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

Unless otherwise defined, all terms (including technical and scientific terms) used herein have the same meaning as commonly understood by one of ordinary skill in the art to which this disclosure belongs.

It should be understood that with respect to any concentration or amount range listed or described herein as being useful, suitable, or the like, it is intended to include every concentration or amount within the range, including the end points, and is to be considered as having been specifically stated. For example, "a range of from 1 to 10" is to be read as indicating each and every possible number along the continuum between 1 and 10. Thus, even if specific data points within the range, or even no data points within the range, are explicitly identified or refer to only a specific few, it is to be understood that the inventors appreciate and understand that any and all data points within the range are to be considered to have been specified, and that the inventors are in possession of the entire range and all points within the range.

All ranges disclosed herein are inclusive of the endpoints, and the endpoints are independently combinable with each other (e.g., ranges of "up to 25 wt %, or, more specifically, 5 wt % to 20 wt %", is inclusive of the endpoints and all intermediate values of the ranges of "5 wt % to 25 wt %," etc.). "Combination" is inclusive of blends, mixtures, alloys, reaction products, and the like. Furthermore, the terms "first," "second," and the like, herein do not denote any order, quantity, or importance, but rather are used to differentiate one element from another. The terms "a" and "an" and "the" herein do not denote a limitation of quantity, and are to be construed to cover both the singular and the plural, unless otherwise indicated herein or clearly contradicted by context. The suffix "(s)" as used herein is intended to include both the singular and the plural of the term that it modifies, thereby including one or more of that term (e.g., the film(s) includes one or more films). Reference throughout the specification to "one embodiment", "another embodiment", "an embodiment", and so forth, means that a particular element (e.g., feature, structure, and/or characteristic) described in connection with the embodiment is included in at least one embodiment described herein, and may or may not be present in other embodiments. In addition, it is to be understood that the described elements may be combined in any suitable manner in the various embodiments. "Or" means "and/or" unless the context specifies otherwise.

Disclosure of a narrower range in addition to a broader range is not a disclaimer of the broader range.

Any and all cited patents, patent applications, and other references are incorporated herein by reference in their entirety. However, if a term in the present application contradicts or conflicts with a term in the incorporated reference, the term from the present application takes precedence over the conflicting term from the incorporated reference.

As used herein, co-impregnating the catalytically active component refers to the impregnating three or more catalytically active components, specifically, four or more catalytically active components, more specifically, five or more catalytically active components, even more specifically, six or more catalytically active components, onto a support in a single impregnation step. It is noted that additional impregnation steps can occur before or after the co-impregnating.

As used herein, catalytic activity can be expressed as the % moles of the hydrocarbon or reactant converted with respect to the moles of hydrocarbon or reactant fed. In propane dehydrogenation where propane is converted to propylene, the catalytic activity can be measured by the propane converted with respect to the moles of propane fed and can be defined by the following formulas:

$$\text{Mole \% Propane Conversion} = [(T_i - T_o)/T_i] \times 100 \quad (1)$$

where, $T_i$, is the number of moles of propane fed and $T_o$ is the number of moles propane unreacted. As used herein, selectivity for propylene can be expressed as:

$$\text{Mole \% Propylene Selectivity} = [X_t/(T_i - T_o)] \times 100 \quad (2)$$

where, $X_t$, is the number of moles of total propylene in the product.

While the disclosure has been described with reference to an exemplary embodiment, it will be understood by those skilled in the art that various changes can be made and equivalents can be substituted for elements thereof without departing from the scope of the disclosure. In addition, many modifications can be made to adapt a particular situation or material to the teachings of the disclosure without departing from the essential scope thereof. Therefore, it is intended that the disclosure not be limited to the particular embodiment disclosed as the best mode contemplated for carrying out this disclosure, but that the disclosure will include all embodiments falling within the scope of the appended claims.

We claim:

1. A method of making a catalyst, comprising
co-impregnating a support with three or more catalytically active components in an impregnating solution to form an impregnated support, wherein the catalytically active component comprises calcium, phosphorus, and nickel; and
calcining the impregnated support to form the catalyst.

2. The method of claim 1, wherein the impregnating solution comprises 0.1 to 5 wt % calcium based upon a total weight of the impregnating solution.

3. The method of claim 1, wherein the catalyst comprises 1 to less than 2 wt % phosphorus based upon a total weight of the catalyst.

4. The method of claim 1, wherein the co-impregnating comprises:
mixing the three or more catalytically active components with water to form the impregnating solution;
contacting a support with the impregnating solution;
impregnating the catalytically active components onto the support to form the impregnated support.

5. The method of claim 4, wherein the catalytically active component comprises elements from one or more of Groups 2, 10, 14, and 15.

6. The method of claim 4, wherein the support comprises a calcined alumina support.

7. The method of claim 4, wherein the total preparation time of the catalyst is 1 to 30 hours.

8. The method of claim 4, wherein the catalyst comprises 0.5 to 1.5 wt % platinum, 1 to 4 wt % tin, 1 to 2 wt % phosphorus; 1 to 5 wt % calcium, 0.12 to 1 wt % chlorine, 0.5 to 2.5 wt % nickel, based upon a total weight of the catalyst.

9. The method of claim 4, wherein the calcining is at a temperature of 200 to 1,000° C. for a total period of 1 to 20 hours.

10. The method of claim 4, wherein the calcining is at a temperature of 500 to 800° C. for a total period of 5 to 15 hours.

11. The method of claim 4, wherein the catalyst is made in a period of less than or equal to 60 hours.

12. The method of claim 4, wherein the catalyst is made in a period of less than or equal to 40 hours.

13. A catalyst formed by the method of claim 1.

14. The method of claim 1, wherein the co-impregnating occurs in less than or equal to 1 hour of forming the impregnating solution.

15. The method of claim 1, wherein the catalytically active component comprises platinum, tin, or a combination comprising at least one of the foregoing.

16. The method of claim 1, wherein the catalyst comprises 0.1 to 20 wt % phosphorus, 0.1 to 75 wt % tin, and 0.1 to 10 wt % of Group 1 and/or 2 metals, based upon a total weight of the catalytically active component(s).

17. The method of claim 1, wherein the catalyst comprises 0.2 to 25 wt % platinum, 0.2 to 5 wt % tin, 1 to 3 wt % phosphorus, 0.1 to 5 wt % calcium, 0.1 to 2 wt % chlorine, and 0.1 to 4 wt % nickel, based upon a total weight of the catalyst.

18. A method of making a catalyst, comprising:
mixing three or more catalytically active components with water to form an impregnating solution;
contacting a support with the impregnating solution;
impregnating the catalytically active components onto the support to form an impregnated support; and
calcining the impregnated support to form the catalyst;
wherein the calcining is performed with a calcination profile, wherein the calcination profile includes increasing a catalyst bed temperature by less than or equal to 10° C./minute to 100° C. and soaking for less than or equal to 10 hours; increasing the catalyst bed temperature by less than or equal to 10° C./minute to 150° C. and soaking for less than or equal to 10 hours; increasing the catalyst bed temperature by less than or equal to 10° C./minute to 340° C.; increasing the catalyst bed temperature by less than or equal to 5° C./minute to 350° C. and soaking for less than or equal to 5 hours; increasing the catalyst bed temperature by less than or equal to 15° C./minute to 540° C.; increasing the catalyst bed temperature by less than or equal to 5° C./minute to 550° C. and soaking for less than or equal to 5 hours.

* * * * *